(12) United States Patent
Hinton et al.

(10) Patent No.: US 6,869,935 B2
(45) Date of Patent: *Mar. 22, 2005

(54) GENE THERAPY FOR PROLIFERATIVE VITREORETINOPATHY

(75) Inventors: David Hinton, Venice, CA (US); W. French Anderson, San Marino, CA (US); Stephen J Ryan, San Marino, CA (US)

(73) Assignee: University of Southern California, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/174,210

(22) Filed: Oct. 16, 1998

(65) Prior Publication Data

US 2003/0191072 A1 Oct. 9, 2003

Related U.S. Application Data

(63) Continuation of application No. 08/630,158, filed on Apr. 10, 1996, now abandoned.

(51) Int. Cl.$^7$ .................. A01N 43/04; C12N 15/63; C12N 15/86; C12N 15/00; C12P 21/06

(52) U.S. Cl. .................. 514/44; 435/455; 435/456; 435/320.1; 435/325; 435/69.1; 800/9

(58) Field of Search .................. 514/44; 435/455, 435/456, 320.1, 325, 69.1; 800/9; 424/93.21

(56) References Cited

FOREIGN PATENT DOCUMENTS

WO   WO 91/15580   10/1991

OTHER PUBLICATIONS

Stedman's Medical Dictionary, 27$^{th}$ Edition (2002–2003), term: neovascularization.*
Chandler et al., Graife's Arch. Clin. Exp. Opthalmol., vol. 224, pp. 86–91, 1986.*
Mullen, C. A., Pharmac. Ther., vol. 63, pp. 199–207, 1994.*
Eck & Wilson, 'Gene-Based Therapy' in Goodman & Gilman's The Pharmacological Basis of Therapeutics, McGraw–Hill: New York, Ninth Edition, pp. 77–101, 1996.*
Sakamoto et al., Opthalmology, vol. 102, pp. 1417–1424, 1995.*
Culver et al., "In Vivo Gene Transfer with Retroviral Vector–Producer Cells for Treatment of Experimental Brain Tumors," Science, vol. 256, Jun. 12, 1992, pp. 1550–1552.
Freeman et al., "The Bystander Effect: Tumor Regression when a Fraction of the Tumor Mass is Genetically Modified", Cancer Research, vol. 53, Nov. 1993, pp. 5274–5283.
Kimura H, Sakamoto T. Cardillo JA, Spee C, Hinton Dr., Gordon EM, Anderson WF, Ryan SJ. Retrovirus–mediated suicide gene transduction in the vitreous cavity of the eye: feasibility in prevention of proliferative vitreoretinopathy, Human Gene Therapy 7:799–808, 1.
Murata T, Hoffmann S, Ishibashi T, Spee C, Gordon EM, Anderson WF, Hinton Dr, Ryan SJ. Retrovirus–mediated gene transfer targeted to retinal photocoagulation sites. Diabetologia 41:500–506, 1998.
Behrens A, Gordon EM, Li L, Liu PX, Chen Z, Peng H, La Bree L, Anderson WF, Hall FL, McDonnell PJ. Retroviral gene therapy vectors for prevention of excimer laser–induced corneal haze. Invest Ophthalmol Vis Sci 43:968–977, 2002.
Gordon EM, Chen ZH, Liu L, Whitely M, Liu L, Wei D, Groshen S, Hinton DR, Anderson WF, Beart RW, Hall FL. Systemic administration of a matrix–targeted retroviral vector is efficacious for cancer gene therapy in mice. Human Gene Therapy 12:193–204, 2001.
Lai C–M, Spilsbury K, Brankov M, Zaknich T, Rakoczy PE. Inhibition of corneal neovascularization by recombinant adenovirus mediated antisense VEGF RNA. Exp Eye Res 75:625–634, 2002.
Lai CM, Shen WY, Constable IJ, Rakoczy PE. Preferential adenovirus–mediated transduction of cells at the sites of laser photocoagulation in the rat eye. Curr Eye Res 19:411–417, 1999.
Shichinohe T, Bochner BH Mizutani K, Nishida M, Hegerich–Gilliam S, Naldini L, Kasahara N. Cancer Gene Therapy 8:879–889, 2001.
Oshima Y, Sakamoto T, Hisatomis T, Tsutsumi C, Ueno H, Ishibashi T. Gene transfer of soluble TGF–beta type II receptor inhibits experimental proliferative vitreoretinopathy. Gene Therapy 9:1214–1220, 2002.
Mori K, Gehlbach P, Ando A, Wahlin K, Gunther V, McVery D, Wei L, Campochiaro PA. Intraocular adenoviral vector–mediated gene transfer on proliferative retinopathies. Invest Ophthalmol Vis Sci 43:1610–1615, 2002.

(List continued on next page.)

Primary Examiner—Deborah Crouch
Assistant Examiner—Thaian N. Ton
(74) Attorney, Agent, or Firm—Fish & Richardson P.C.

(57) ABSTRACT

A method of treating ocular disorders (such as, for example, proliferative vitreoretinopathy or PVR) associated with replicating ocular cells by transfecting replicating ocular cells in vivo with a polynucleotide encoding an agent which is capable of providing for the inhibition, prevention, or destruction of the growth of the replicating ocular cells upon expression of the agent. The agent may be a viral thymidine kinase, and the polynucleotide encoding the agent may be contained in a retroviral vector. Once the replicating ocular cells are transduced with the retroviral vector, the patient is given a chemotherapeutic or interaction agent, such as ganciclovir, which kills the transfected replicating ocular cells.

13 Claims, 8 Drawing Sheets

OTHER PUBLICATIONS

Lynch CM, Hara PS, Leonard JC, Williams JK, Dean RH, Geary RL. Adeno–associated virus vectors for vascular gene delivery. Circ Res 80:497–505, 1997.

Teramoto S, Ishii T, Matsuse T. Variables pertinent to the efficiency of adeno–associated virus (AAV) vectors mediated gene transfer to human vascular endothelial cells. Hypertesnion Res 24:437–443, 2001.

Auricchio A, Behling KC, Maguire AM, O'Conner EE, Bennett J, Wilson JM, Tolentino MJ. Inhibition of retinal neovascularization by intraocular viral–mediated delivery of anti–angiogenic agents. Mol Therapy 6:490–494, 2002.

Igarashi T, Miyake K, Kato K, Watanabe A, Ishizaki M, Ohara K, Shimada T. Lentivirus–mediated expression of angiostatin efficiently inhibits neovascularization in a murine proliferative retinopathy model. Gene Therapy 10:219–226, 2003.

Murthy RC, McFarland TJ, Yoken J, Chen S, Barone C, Burke D, Zhang Y, Appukuttan B, Stout JT. Corneal transduction to inhibit angiogenesis and graft failure. Invest Ophthalmol Vis Sci 44:1837–1842, 2003.

Bennett J, Maguire AM. Gene Therapy for Ocular Disease. Molec Ther 1:501–504, 2002.

Murata T, Kimura H, Sakamoto T, Osusky R, Spee C. Stout TJ, Hinton DR, Ryan SJ. Ocular gene therapy: experimental studies and clinical possibilities. Ophthal Res 29:242–251, 1997.

Sakamoto, et al., *Investigative Opthomology and Visual Science*, vol. 35, No. 4, Abstract 2391–74 (Mar. 15, 1994).

Sakamoto, et al., ARVO Abstract (Mar. 1995).

Kimura, et al., Gene Therapy Steamboat Abstract (1995).

Spec, et al, Gene Therapy Steamboat Abstract (1995).

Charteris, *Br. J. Opthomol.* vol. 79, pp. 953–960 (1995).

Sakamoto, et al., *Opthomology*, vol. 102, No. 10, pp. 1417–1424 (Oct. 1995).

Stout, *Opthomology*, vol. 104, No. 10, pp. 1415–1416 (Oct. 1995).

Kimura, et al., ARVO Abstract (Mar. 1996).

Schubert, et al., ARVO Abstract (Mar. 1996).

Mullen, *Pharmac. Ther.* vol. 63, pp. 199–207 (1994).

Culver, et al., T.I.G., vol. 10, No. 5, pp. 174–178 (1994).

Marshall, *Science*, vol. 269, pp. 1050–1055 (1995).

Miller, et al., *FASEB*, vol. 9, pp. 190–199 (1995).

Li, et al., *Investigative Opthomology & Visual Science*, vol. 35, No. 5, pp. 2543–2549 (Apr. 1994).

Orkin, et al., *Report and Recommendations* (Dec. 7, 1995).

Ledley, *Haman Gene Therapy*, vol. 2, pp. 77–83 (1991).

\* cited by examiner

GENE THERAPY FOR PROLIFERATIVE VITREORETINOPATHY

This is a Continuation of application Ser. No. 08/630,158 filed Apr. 10, 1996 now abandoned.

This invention relates to gene therapy for treating ocular disorders involving intraocular cellular proliferation, such as, for example, proliferative vitreoretinopathy or PVR. More particularly, this invention relates to the treatment of ocular disorders associated with intraocular cellular proliferation, such as proliferative vitreoretinopathy, by transducing replicating ocular cells with a polynucleotide encoding an agent which is capable of providing for the inhibition, prevention, or destruction of the growth of the replicating ocular cells. The agent may be a negative selective marker, such as, for example, a viral thymidine kinase. Such transduction then may be followed by the administration of an interaction agent, such as, for example, ganciclovir or acyclovir, thereby killing the replicating ocular cells.

BACKGROUND OF THE INVENTION

One of the most common causes of retinal detachment is proliferative vitreoretinopathy, an intraocular, non-malignant cellular proliferation. This process results ultimately in a separation of the retina from the retinal pigment epithelium, or RPE, because of tractional forces applied directly to the inner and outer retinal surfaces. This is the major cause for failure of retinal re-attachment surgery. (*Ophthalmology*, Vol. 90, pgs. 121–123 (1983)).

Proliferative vitreoretinopathy is characterized by the formation of contractile cellular membranes on both sides of the retina. (Clarkson, et al., *Am. J. Ophthalmol.*, Vol. 84, pgs. 1–17 (1977); Constable, *Trans. Ophthalmol. Soc. U.K.*, Vol. 95, pgs. 382–386 (1975); Constable, et al., *Retina Congress*, Pruett, et al., eds., pgs. 245–257, Appleton-Century-Crofts, New York (1972); Daicker, et al., *Graefe's Arch. Klin. Exp. Ophthalmol.*, Vol. 210, pgs. 109–120 (1979); Fastenberg, et al., *Am. J. Ophthalmol.*, Vol. 93, pgs. 565–572 (1982); Glaser, et al., *Ophthalmology*, Vol 94, pgs. 327–332 (1987); Green, et al., *Trans. Ophthalmol. Soc. U.K.*, Vol. 99, pgs. 63–77 (1979); Kampik, et al., *Arch. Ophthalmol.*, Vol. 99, pgs. 1445–1454 (1981); Machemer, et al., *Am. J. Ophthalmol.*, Vol. 85, pgs. 181–191 (1978)). While the pathobiology of proliferative vitreoretinopathy is not clear, it appears that RPE cells are key to the development of these membranes. (Green, et al., 1979; Kampik, et al., 1981; Machemer, et al., 1978; Laqua, et al., *Am. J. Ophthalmol.*, Vol. 80, pgs. 602–618 (1975); Hiscott, et al., *Br. J. Ophthalmol.*, Vol. 68, pgs. 708–715 (1984)). A large body of evidence supports the concept that previously quiescent RPE cells, when displaced into the vitreous cavity and exposed to the appropriate combination of cytokines, will divide and differentiate. This differentiation results in cells having myofibroblastic characteristics including adhesiveness and contractility. As these membranes form tight adhesions with the retinal surfaces, tractional forces are generated and detachment ensues.

Most evidence indicates retinal tears as the pathway through which RPE cells move in order to enter the vitreous cavity. (Hiscott, et al., 1984), and there is a clear association between the size of a retinal tear and the incidence of proliferative vitreoretinopathy. (Ryan, *Am. J. Ophthalmol.*, Vol. 100, pgs. 188–193 (1985)). Most likely, the RPE cells remain attached to the retinal flap as the retina is displaced into the vitreous cavity or are introduced into the vitreous cavity following cryotherapy of the retina and RPE during retinal detachment repair. (Yoshizumi, et al., *Retinal Diseases*, Ryan, et al., eds., New York, Grune & Stratton (1984); Campochiaro, et al., *Arch. Ophthalmol.*, Vol. 103, pgs. 434–436 (1985); Hilton, et al., *Arch. Ophthalmol.*, Vol. 91, pgs. 445–450 (1974)).

Viable retinal pigment epithelial cells, displaced into the vitreous cavity, are exposed to a wide variety of proteins, cytokines, and chemoattractants. Extracellular matrix proteins have profound effects on cell morphology and behavior (Glaser, et al., *Ophthalmology*, Vol. 100, pgs. 466–470 (1993)). RPE cells, when exposed in vitro to the extracellular matrix proteins and collagensi found in the vitreous, change from their typical epithelial cell morphology to a mesenchymal or fibroblast-like morphology. (Kampik, et al., 1981; Hay, et al., *Cell Biology of Extracellular Matrix*, New York, Plenum Press (1982); Vidaurri-Leal, et al., *Arch. Ophthalmol.*, Vol. 102, pgs. 1220–1223 (1984); Laqua, et al., *Am. J. Ophthalmol.*, Vol. 80, pgs. 913–929 (1975); Machemer, et al., *Am. J. Ophthalmol.*, Vol. 80, pgs. 1–23 (1975)).

While considerable data regarding the RPE cell's role in proliferative vitreoretinopathy has been gathered, other cells also are involved. (Campochiaro, et al., *Arch. Ophthalmol.*, Vol. 103, pgs. 1403–1405 (1985); Van Horn, et al., *Am. J. Ophthalmol.*, Vol. 84, pgs. 383–393 (1977); Hiscott, et al., *Br. J. Ophthalmol.*, Vol. 68, pgs. 698–707 (1984)). Glial cells, monocytes, and macrophages are seen in immunohistopathologic preparations of membranes removed from patients with proliferative vitreoretinopathy. Recent evidence suggests that a cellular-signaling dialogue can occur between these divergent cell types whereby cells release cytokines which induce the production of cell surface receptors for a variety of growth factors on neighboring cells. (Campochiaro, et al., *Arch. Ophthalmol.*, Vol. 102, pgs. 1830–1833 (1984); Campochiaro, et al., *Arch. Ophthalmol.*, Vol. 103, pgs. 576–579 (1985); Yamada, *Ann. Rev. Biochem.*, Vol. 52, pgs. 761–799 (1983); Connor, et al., *Invest. Ophthalmol. Vis. Sci.*, Vol. 29, pg. 307 (1988)). The cells become responsive to these new factors, and thus behave differently and differentiate further. Morphologically, each of these cell types is found intimately apposed to other cell types in these membranes.

In summary, proliferative vitreoretinopathy is a process of cellular proliferation which, if left unchecked, ultimately will result in a detachment of the retina from the RPE. This process takes place within the eye, where cell division normally does not occur after completion of development. A variety of cell types is involved, including RPE cells, glial cells, monocytes, and macrophages. The pathobiology of proliferative vitreoretinopathy, while not understood completely, involves the exposure of previously quiescent cells to factors which promote abnormal differentiation and cell division. This differentiation results in adhesive cells which contract in an unregulated, disorganized fashion and produce the tractional forces which detach the retina.

The current treatment for PVR is vitreoretinal surgery. Although such treatment often is successful, recurrent vitreoretinal traction may result in redetachment. The resulting retinal detachment sometimes causes permanent impairment of visual function. Thus, pharmacologic and other forms of therapy to inhibit recurrent membrane formation are needed.

Retroviral vectors including a negative selective marker, in particular the Herpes Simplex Virus thymidine kinase (HSV-TK) gene, have been used for treating tumors. (Moolten, et al., *J. Nat. Cancer Inst.*, Vol. 82, pgs. 297–300 (1990); Moolten, et al., *Human Gene Therapy*, Vol. 1, pgs.

125–134 (1990); Plautz, et al., *New Biologist*, Vol. 3, pgs. 709–715 (1991); Culver, et al., *Science*, Vol. 256, pgs. 1550–1552 (1992); Ram, et al., *J. Neurosurg.*, Vol. 81, pgs. 256–260 (1994)). Herpes Simplex Virus thymidine kinase confers sensitivity to the guanosine analogue, ganciclovir, which inhibits DNA synthesis and eliminates proliferating cells. (Smith, et al., *Antimicrob. Agents Chemother.*, Vol. 22, pgs. 55–61 (1982); Field, et al., *Proc. Nat. Acad. Sci.*, Vol. 80, pgs. 4139–4143 (1983)). It has been demonstrated that experimental PVR induced in rabbits by intraocular injection of fibroblasts bearing the HSV-TK gene was inhibited by treatment with ganciclovir (Sakamoto, et al., *Ophthalmology*, Vol. 102, pgs. 1417–1424 (1995)).

It has been reported that HSV-TK transduced cells are toxic to nearby nontransduced cells that were resistant to ganciclovir. Such phenomenon is termed the "bystander effect." (Culver, et al., 1992; Ram, et al., *Cancer Research*, Vol. 53, pgs. 83–88 (1993); Freeman, et al., *Cancer Research*, Vol. 53, pgs. 5247–5283 (1993)). Sakamoto, et al., (1995) also showed a significant bystander effect in their work with experimental PVR in the rabbit model.

SUMMARY OF THE INVENTION

Applicants have discovered that one may administer to the vitreous cavity of the eye an expression vehicle, such as, for example, a viral vector such as a retroviral vector, containing a desired polynucleotide sequence, and that such expression vehicle is not inactivated and transfects replicating ocular cells. Thus, Applicants' invention is directed to the treatment of ocular disorders such as proliferative vitreoretinopathy by transfecting replicating ocular cells in vivo with a polynucleotide encoding an agent which is capable of providing for the inhibition, prevention, or destruction of the growth of such replicating ocular cells upon expression of the agent. The transfection of such cells in vivo may be achieved by administering to the vitreous cavity of the eye of a patient an appropriate expression vehicle, such as, for example, a viral vector, which includes the polynucleotide encoding the agent.

BRIEF DESCRIPTION OF THE DRAWINGS

The invention now will be described with respect to the drawings, wherein:

FIGS. 5A, 5B, 5C, and 5D show the stages of PVR at 4 days, 7 days, 14 days, and 28 days, respectively, following ganciclovir treatment.

DETAILED DESCRIPTION OF THE INVENTION

Figure 1:
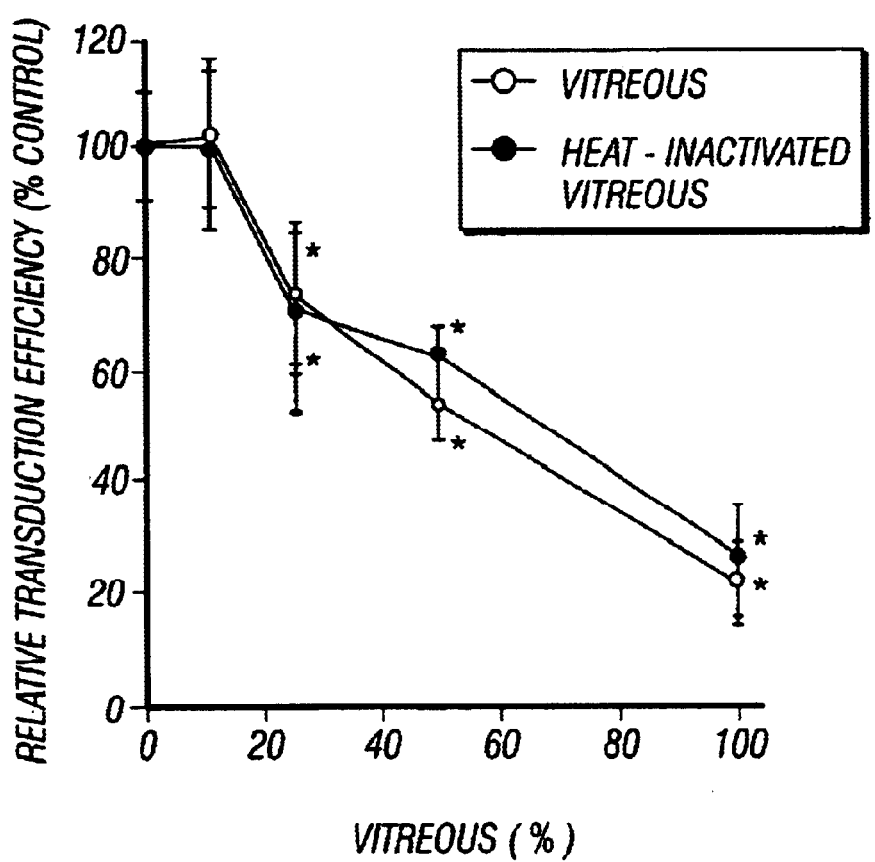
FIG. 1 is a graph depicting the transduction efficiency of the G1BgSvNa retroviral vector in the presence of varying concentrations of vitreous from the eyes of rabbits.

In accordance with an aspect of the present invention, there is provided a method of treating an ocular disorder involving intraocular cellular proliferation. The method comprises transfecting replicating ocular cells in a host in vivo with a polynucleotide encoding an agent which is capable of providing for the inhibition, prevention, or destruction of the growth of the replicating ocular cells upon expression of the polynucleotide encoding the agent.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

The polynucleotide encoding the agent which is capable of providing for the inhibition, prevention, or destruction of the growth of the replicating ocular cells may be contained within an appropriate expression vehicle which is transduced into the replicating ocular cells. Such expression vectors include, but are not limited to, eukaryotic vectors, prokaryotic vectors (such as, for example, bacterial vectors), and viral vectors.

In one alternative embodiment, the polynucleotide encoding the agent, or an expression vehicle containing the polynucleotide encoding the agent, is contained within a liposome.

In one preferred embodiment, the vector is a viral vector. Viral vectors which may be employed include DNA virus vectors (such as adenoviral vectors, adeno-associated virus vectors, Herpes Virus vectors, and vaccinia virus vectors), and RNA virus vectors (such as retroviral vectors). When an RNA virus vector is employed, in constructing the vector, the polynucleotide encoding the agent is in the form of RNA. When a DNA virus vector is employed, in constructing the vector, the polynucleotide encoding the agent is in the form of DNA.

In a particularly preferred embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. The vector is preferably an infectious, replication incompetent retrovirus particle.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art.

The removal of the gag, pol and env genes results in a vector backbone, comprised of a 5' LTR, a packaging signal, one or more cloning sites, into which the heterologous gene or genes of interest can be introduced, and a 3' LTR. The preferred vector backbone is the G1 vector backbone, which is disclosed in McLachlin, et al., *Virology*, 195:1–5 (1993) and in PCT patent application no. WO 91/10728 for "Novel Retroviral Vectors," published on Jul. 25, 1991.

The heterologous gene or genes are incorporated into the proviral backbone by standard techniques to form the retroviral vector. Techniques for the preparation of retroviral vectors are disclosed in PCT application WO 91/10728 as well as the following articles: Armentano, et al., *J. Virol.*, 61:1647–1650 (1987), Bender, et al., *J. Virol.*, 61:1639–1646 (1987), and Miller, et al., *Biotechniques*, 7:980–990 (1989). The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Suitable promoters include the SV40 promoter, the human cytomegalovirus (CMV) promoter, the beta-actin promoter, the alpha fetoprotein promoter, and any promoter naturally associated with any heterologous gene of interest.

The retroviral vectors may be in the form of a plasmid, a segment of viral RNA, or a segment of proviral DNA. For the present invention, the preferred retroviral vector is G1TK1SvNa, which is disclosed in PCT patent application WO 95/06486, published on Mar. 9, 1995, entitled Treatment of Human Tumors by Genetic Transformation of Human Tumor Cells.

The retroviral vector is introduced into a packaging cell to form a producer cell. Packaging cells provide the gag, pol, and env genes in trans, which permits the packaging of the retroviral vector into a recombinant retrovirus that is infectious but replication defective. The vectors are transferred into the packaging cells by standard gene transfer techniques, which include transfection, transduction, calcium phosphate precipitation, electroporation, and liposome-mediated DNA transfer. Examples of packaging cells that may be used include, but are not limited to, the PE501, PA317, Psi-2, Psi-AM, PA12, T19-14X, VT-19-17-H2, Psi-CRE, Psi-CRIP, GP+E-86, GP+envAM12, and DAN cell lines. A preferred producer cell line for the present invention for the production of recombinant retrovirus is the producer cell line designated PA317/G1TK1SvNa, which is disclosed in PCT application WO 95/06486.

The retroviral vectors are administered to the host in an amount effective to inhibit, prevent, or destroy the growth of the replicating ocular cells. The host may be a mammalian host, including human and non-human primate hosts. Such administration may be by direct administration of the retroviral vectors to the vitreous cavity of the eye of the host, or to the subretinal space of the eye, or to the anterior chamber of the eye, whereby the retroviral vectors transduce the replicating ocular cells. The locus of administration of the retroviral vectors is dependent upon factors which include the nature of the ocular disorder being treated. In general, the retroviral vectors are administered in the eye in an amount of at least $10^4$ cfu/dose, and in general, such amount does not exceed $10^8$ cfu/dose. Preferably, the retroviral vectors are administered in an amount of from about $10^5$ cfu/dose to about $10^7$ cfu/dose. The exact dosage is dependent upon a variety of factors, which may include the age, weight, and sex of the patient, the nature of the ocular disorder being treated, and the severity of the ocular disorder being treated.

The retroviral vectors also may be administered in conjunction with an acceptable pharmaceutical carrier, such as, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.). The selection of a suitable pharmaceutical carrier is deemed to be apparent to those skilled in the art from the teachings contained herein.

In one embodiment, the agent which is capable of providing for the inhibition, prevention, or destruction of the growth of the replicating ocular cells is a negative selective marker; i.e., a material which in combination with a chemotherapeutic or interaction agent inhibits, prevents, or destroys the growth of the replicating ocular cells.

In a preferred embodiment, the negative selective marker is a viral thymidine kinase selected from the group consisting of Herpes Simplex Virus thymidine kinase, cytomegalovirus thymidine kinase, and varicella-zoster virus thymidine kinase. When such viral thymidine kinases are employed, the interaction or chemotherapeutic agent preferably is a nucleoside analogue, for example, one selected from the group consisting of ganciclovir, acyclovir, and 1-2-deoxy-2-fluoro-β-D-arabinofuranosil-5-iodouracil (FIAU). Such interaction agents are utilized efficiently by the viral thymidine kinases as substrates, and such interaction agents thus are incorporated lethally into the DNA of the replicating ocular cells expressing the viral thymidine kinases, thereby resulting in the death of the replicating ocular cells.

In another embodiment, the negative selective marker is cytosine deaminase. When cytosine deaminase is the negative selective marker, a preferred interaction agent is 5-fluorocytosine. Cytosine deaminase converts 5-fluorocytosine to 5-fluorouracil, which is highly cytotoxic. Thus, the replicating ocular cells which express the cytosine deaminase gene convert the 5-fluorocytosine to 5-fluorouracil and are killed.

The interaction agent is administered in an amount effective to inhibit, prevent, or destroy the growth of the transduced replicating ocular cells. The interaction agent preferably is administered intraocularly, such as, for example, by injection into the vitreous cavity, the subretinal space, or the anterior chamber. In general, the interaction agent is administered intraocularly in an amount up to 1 mg/eye/dose, preferably from 20 μg/eye/dose to 1 mg/eye/dose, depending on overall toxicity to a patient. Alternatively, the interaction agent is administered intravenously. When administered intravenously, the interaction agent in general is administered in an amount of at least 5 mg/kg of body weight and which does not exceed 10 mg/kg of body weight, depending on overall toxicity to a patient.

When an expression vehicle, such as those hereinabove described, including a negative selective marker is administered to replicating ocular cells, a "bystander effect" may result, i.e., replicating ocular cells which were not originally transduced with the nucleic acid sequence encoding the negative selective marker may be killed upon administration of the interaction agent. Although Applicants do not intend to be limited to any theoretical reasoning, the transformed replicating ocular cells may be producing a diffusible form of the negative selective marker that either acts extracellularly upon the interaction agent, or is taken up by adjacent, non-transduced replicating ocular cells, which then become susceptible to the action of the interaction agent. It also is possible that one or both of the negative selective marker and the interaction agent are communicated between replicating ocular cells.

Ocular disorders which may be treated include proliferative vitreoretinopathy; as well as ocular disorders associated with neovascularization; including diabetic retinopathy, retinopathy of prematurity, age-related macular degeneration, and neovascular glaucoma; and epithelial cell proliferation such as lens capsule epithelial cell proliferation.

When the method of the present invention is employed in treating proliferative vitreoretinopathy, the cells which are transduced with the polynucleotide encoding the agent, include replicating ocular cells found in the contractile cellular membranes on both sides of the retina, such membranes being characteristic of proliferative vitreoretinopathy. Such replicating ocular cells include, but are not limited to, retinal pigment epithelial (RPE) cells, glial cells, fibroblasts, fibrocytes, macrophages, and pericytes found in the contractile cellular membranes.

In a preferred embodiment, proliferative vitreoretinopathy may be treated by administering, preferably by injection, to the vitreous cavity of the eye of a patient retroviral vectors including a polynucleotide encoding a negative selective marker. Applicants have found that, when retroviral vectors are administered to the vitreous cavity of the eye, such vectors are not deactivated and will transduce replicating ocular cells. Thus, the retroviral vectors including the polynucleotide encoding a negative selective marker transduce replicating ocular cells found in the contractile cellular membranes on both sides of the retina. Such cells include retinal pigment epithelial cells, glial cells, fibroblasts, and fibrocytes as hereinabove described.

Subsequent to the administration of the retroviral vectors to the vitreous cavity, a chemotherapeutic or interaction agent is administered to the vitreous cavity of the eye, whereby the replicating ocular cells in the contractile cellular membranes are killed.

Alternatively, in the treatment of proliferative vitreoretinopathy, the retroviral vectors and the interaction agent may be administered to the subretinal space.

When the method of the present invention is employed to treat retinopathy, such as diabetic retinopathy or retinopathy of prematurity, the cells which are transduced with the polynucleotide encoding the agent include replicating cells found in blood vessels in the retina.

In one embodiment, the retinopathy may be treated by administering to the vitreous cavity of the eye of a patient retroviral vectors including a polynucleotide encoding a negative selective marker. The retroviral vectors including the polynucleotide encoding a negative selective marker transduce replicating cells found in blood vessels of the retina. After such retroviral vectors are administered to the vitreous cavity, a chemotherapeutic agent or interaction agent is administered to the vitreous cavity, whereby the replicating cells found in the blood vessels of the retina are killed.

When the method of the present invention is employed to treat macular degeneration with subretinal neovascularization, the disorder may be treated by administering the retroviral vectors including a polynucleotide encoding a negative selective marker to the subretinal space. The retroviral vectors including the polynucleotide encoding a negative selective marker transduce replicating cells including endothelial cells, retinal pigment epithelial cells, pericytes, glial cells, and macrophages. After the retroviral vectors are administered to the subretinal space, a chemotherapeutic agent or interaction agent is administered to the subretinal space, whereby the replicating cells are killed.

The method of the present invention also may be employed to treat neovascular glaucoma by administering the retroviral vectors including a negative selective marker to the anterior chamber of the eye. The retroviral vectors then transduce replicating cells found in blood vessels in the anterior chamber. After the retroviral vectors are administered to the anterior chamber of the eye, a chemotherapeutic or interaction agent is administered to the anterior chamber, whereby the replicating cells found in blood vessels in the anterior chamber of the eye are killed.

In addition, the method of the present invention may be employed to treat lens capsule epithelial cell proliferation. The retroviral vectors including a polynucleotide encoding a negative selective marker are administered to the anterior chamber of the eye, whereby the retroviral vectors transduce proliferating lens epithelial cells. Subsequent to the administration of the retroviral vectors to the anterior chamber, a chemotherapeutic or interaction agent is administered to the anterior chamber, whereby the transduced lens epithelial cells are killed.

EXAMPLES

The invention now will be described with respect to the following examples; however, the scope of the present invention is not intended to be limited thereby.

For the following Examples 1 through 6, rabbit dermal fibroblasts (RAF's) were collected and cultured as described in Wiedemann, et al., *Exp. Eye Res.*, Vol. 41, pgs. 619–628 (1985).

Cells were maintained with Dulbecco's modified Eagle's medium (DMEM, Irvine Scientific, Santa Ana, Calif.) containing 10% fetal calf serum (FCS, Irvine Scientific), 100 $\mu$g/ml streptomycin (Sigma Chemical Co., St. Louis, Mo.), 100 $\mu$g/ml penicillin (Sigma Chemical Co.), and 200 $\mu$M L-glutamine (Sigma Chemical Co.) [DMEM-10]. The third to eighth passaged cells were used in these studies.

The $\mu$-galactosidase and Herpes Simplex Virus thymidine kinase expression vectors were provided as high titer PA317 packaging cell clones [titers, $1.3 \times 10^6$ and $4.9 \times 10^6$ G418$^r$ colony forming units (cfu)/ml for $\beta$-galactosidase and Herpes Simplex Virus thymidine kinase expression vectors, respectively] by Genetic Therapy, Inc., Gaithersburg, Md. These vectors were named G1BgSvNa and G1Tk1SvNa, respectively, to indicate the order of promoters and coding regions contained in the vector (G1, MoMuLV LTR; Bg, $\beta$-galactosidase gene; Tk, herpes simplex virus thymidine kinase gene; Sv, SV40 early region enhancer/promoter; Na, neo$^r$ gene). The vector source, G1XSvNa containing only the SV40 promoter-drive neo$^r$ gene, was used as a control. G1Tk1SvNa and G1XSvNa were concentrated by ultracentrifugation to a titer of $1-2 \times 10^8$ cfu/ml after collection in UltraDOMA (Biowhittaker, Walkersville, Md.) serum-free medium. Retroviral vector G1Tk1SvNa is described further in PCT Application No. WO95/09654, published Apr. 13, 1995. Retroviral vector G1BgSvNa was generated from the plasmid pG1BgSvNa. pG1BgSvNa was constructed by digesting pSvNa (PCT Application No. WO95/09654) and pG1Bg (PCT Application No. WO91/10728) with SalI and HindIII. The SalI-HindIII fragment of pSvNa containing the SV40 promoter and a neomycin resistance gene was ligated to the SalI/HindIII digested pG1Bg to form pG1BgSvNa. All producer cell lines tested negative for replication-competent virus.

Rabbit dermal fibroblasts were transduced in the presence of 8 µg/ml Polybrene (Gibco, Life Technologies, Grand Island, N.Y.) with 1 ml of either G1BgSvNa or G1Tk1SvNa supernatant for 2 hr at 37° C. After 2 hr, 10 ml of fresh medium was added; the cells were incubated overnight, and the medium was changed the next day. Forty-eight hours after transduction, cells were split 1:5 and treated with 0.8 mg/ml G418 (Gibco, Life Technologies), a neomycin analog. The concentration of G418 (0.8 mg/ml) that would be toxic to nontransduced RDFs was determined previously. The lacZ or HSV-tk transduced RDFs were selected for two weeks in medium containing G418.

Example 1

Effect of Vitreous Humor on in vitro Transduction

Rabbit dermal fibroblasts were plated at $2.5 \times 10^4$ cells/well in 6-well plates (Corning, New York, N.Y.) and incubated overnight at 37° C. in 5% $CO_2$. G1BgSvNa supernatant ($1.3 \times 10^6$ cfu/ml) was used for transduction in vitro. The multiplicity of infection (MOI), or vector particle/target cell ratio was 52. A tenfold serial dilution of vector supernatants ($10^{-2}$, $10^{-3}$, $10^{-4}$) containing 10%, 25%, 50% and 100% rabbit vitreous humor (with or without heating for 30 minutes at 56° C.) or 10% heat-inactivated fetal calf serum (FCS) as a control and 8 µg/ml Polybrene was added to all wells on day 2. The final volume of each well was 1 ml. After 2 hr of incubation, 4 ml of fresh DMEM-10 was added and the wells were incubated for an additional 22 hr at 37° C. in 5% $CO_2$. On day 3, the medium was removed and replaced with DMEM-10 containing 800 µg/ml G418. Plates were incubated at 37° C. in 5% $CO_2$. On days 6, 9 and 12, plates were replenished with fresh medium containing 800 µg/ml G418. On day 14, colonies were stained with X-gal and the transduction efficiency was calculated. Cells from the third to eighth passages were used. Each experiment was performed in triplicate.

The vitreous was collected without macroscopic contamination by iridal, uveal or retinal tissue by expressing it from enucleated rabbit eyes (Pel-Freez Biochemicals, Rogers, Ak.) after removal of the cornea, aqueous and lens. The vitreous was homogenized on ice, using a cell disrupter, and sterilized by passage through a filter with a pore size of 0.22 µm.

As shown in FIG. 1, the vitreous humor dose-dependently inhibited the transduction. Although there was no significant difference between the transduction efficiency with 10% vitreous humor and the control (with 10% FCS), higher concentrations of vitreous humor significantly inhibited transduction. Transduction efficiency with 100% vitreous humor was reduced to 25% of control. There was no difference between the transduction efficiency of vitreous humor with and without heat inactivation.

Example 2

In vitro Sensitivity of HSV-tk Transduced Cells to Ganciclovir

The sensitivity of HSV-tk positive RDFs (100% HSV-tk transduced RDFs) and HSV-tk negative RDFs to ganciclovir was determined by using a tetrazolium-based calorimetric assay (XTT assay) (Scudiero et al., *Cancer Research*, Vol. 48, pgs. 4827–4833 (1988); Roehm et al., *J. Immunol. Methods*, Vol. 142, pgs. 257–265 (1991)). HSV-tk positive RDFs and HSV-tk negative RDFs were seeded at a density of $5 \times 10^3$ cells/well of 96-well culture plates (Corning) and incubated with DMEM-10 at 37° C. in 5% $CO_2$ overnight. Then cells were treated with DMEM-10 containing various concentrations of ganciclovir (GCV; Cytovene; Syntex Inc., Palo Alto, Calif.) or only DMEM-10. After a total of 72 hr incubation, XTT assay was performed using a kit (cell proliferation II; Boehringer Mannheim, Indianapolis, Ind.). The results were read on a microplate reader (MR700; Dynatech Laboratories, Inc., Chantilly, Va.).

Ganciclovir inhibited HSV-tk positive RDFs in a dose-dependent manner. At a concentration range of 0.001–50 µg/ml, ganciclovir showed no significant toxicity to HSV-tk negative RDFs while demonstrating toxicity to HSV-tk positive RDFs. After 72 hr of incubation with ganciclovir, the $IC_{50}$ (defined as a concentration required for 50% cytotoxicity) of this clone of HSV-tk positive RDFs was 0.1 µg/ml.

Example 3

In vitro Bystander Effect

To determine the cytotoxic effect of a small number of HSV-tk positive cells on neighboring HSV-tk-negative cells, cocultures of HSV-tk positive cells and HSV-tk-negative cells were performed by mixing these two cells in varying proportions. Briefly, mixtures of HSV-tk-positive and -negative RDFs ($2.0 \times 10^4$ cells/well) were seeded at various mixing ratios (0, 1.0, 2.5, 5.0, 10, and 100% HSV-tk-positive cells of total cells) in 24-well culture plates (Corning) and incubated at 37° C. in 5% $CO_2$ overnight. Cells were then treated with 1 µg/ml ganciclovir for 3, 5, and 7 days. The number of cells was counted with a Coulter counter (Coulter Electronics, Inc., Hialeah, Fla.).

Figure 2A:
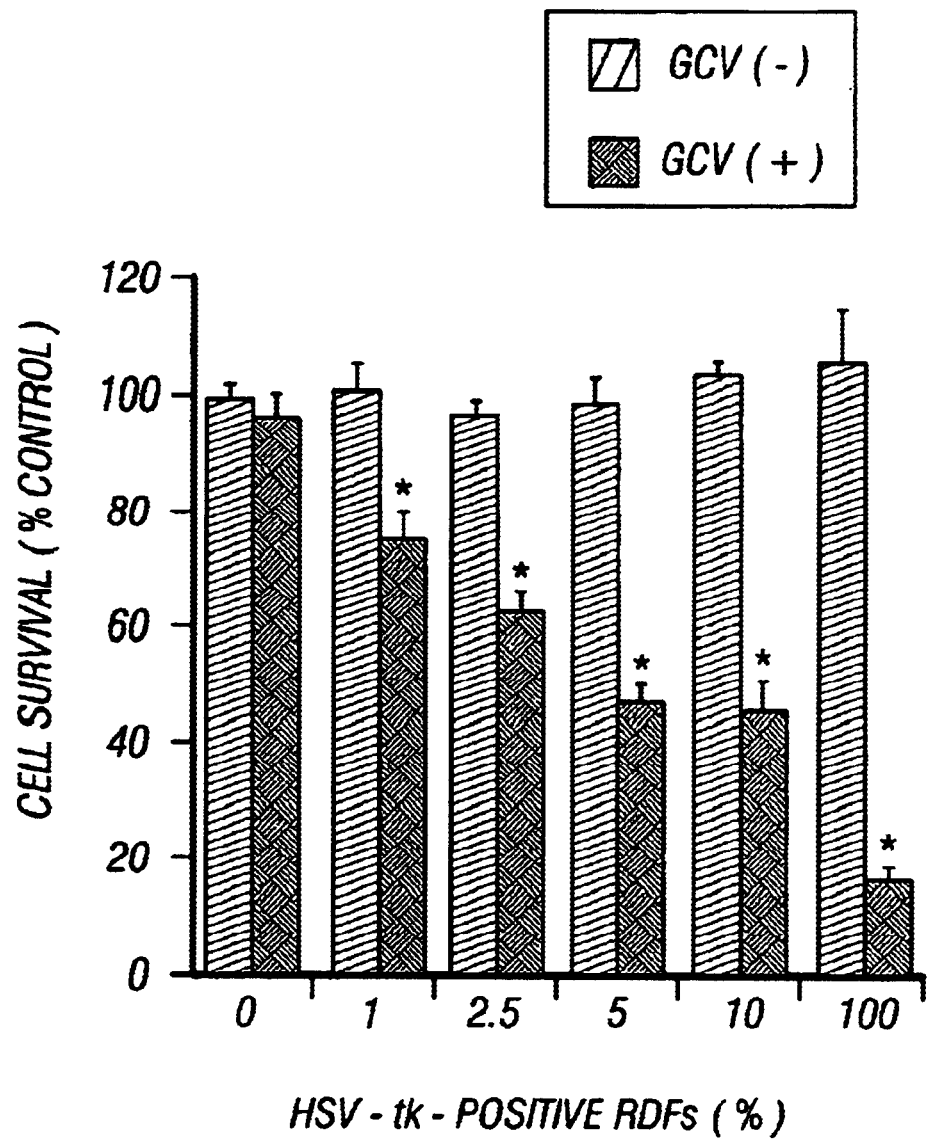
FIG. 2A is a graph of the number of cells in cultures having various proportions of HSV-tk positive and HSV-tk negative rabbit dermal fibroblasts three days after exposure to ganciclovir.
Figure 2B:
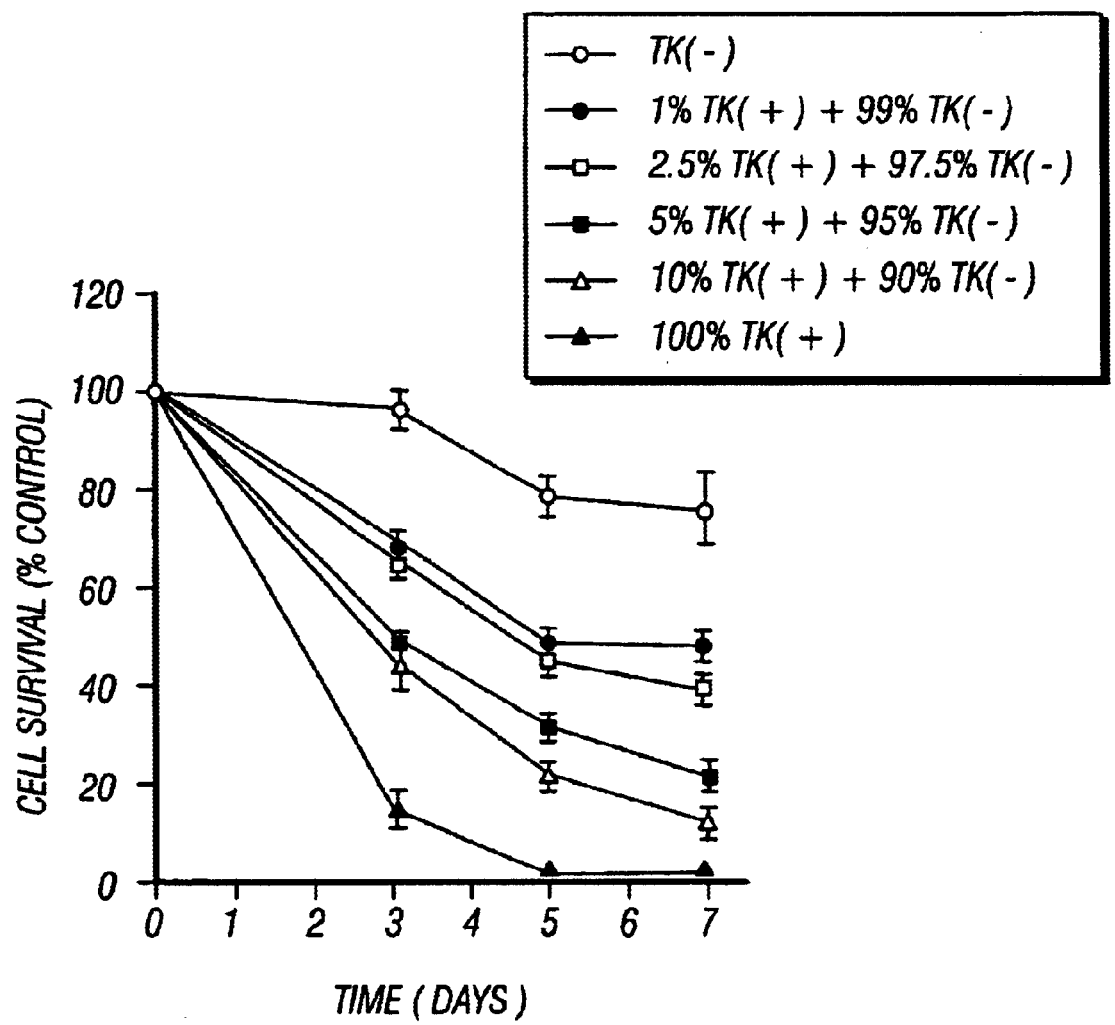
FIG. 2B is a graph of the survival of cells in cultures having various proportions of HSV-tk positive and HSV-tk negative dermal fibroblasts for up to seven days after exposure to ganciclovir.

After 3 days of incubation, ganciclovir inhibited proliferation of co-culturing cells. The inhibitory effect depended on the percentage of total cells that were HSV-tk positive (FIG. 2A). HSV-tk positive RDFs showed a toxic effect on HSV-tk-negative RDFs even in a co-culture of 1% HSV-tk positive RDFs and 99% HSV-tk negative RDFs. This indicated that a bystander effect contributed to the cytotoxic effect of GCV on HSV-tk negative RDFs when mixed with HSV-tk positive RDFs. Ganciclovir induced cytotoxicity of HSV-tk positive cells was time-dependent (FIG. 2B). As shown in FIG. 2B, an asterisk indicates a significant difference between treatment with ganciclovir and without ganciclovir. The doubling time of HSV-tk negative RDFs in DMEM-10 without ganciclovir was approximately 1.4 days.

Example 4

In vivo Transduction with G1BgSvNa

The right eye was used from each of 15 New Zealand white rabbits of both sexes; each rabbit weighed between 2.5 and 3.5 kg. All procedures were approved by the University of Southern California Institutional Care and Use Committee and were in accordance with the NIH Guide for the Care and Use of Laboratory Animals. The animals were anesthetized with a mixture (4:1) of ketamine hydrochloride (24 mg/kg) and xylazine hydrochloride (6 mg/kg) and pupils were dilated with 1% tropicamide and 2.5% phenylephrine hydrochloride eyedrops. The ocular surface was then anesthetized with topical instillation of 0.5% proparacaine hydrochloride eyedrops.

A limbal conjunctival incision was made in the right eye of each animal. The sclera was exposed, and two 1-mm sclerotomies were made with a microsurgical vitreal retinal blade, 2 mm from the limbus, using a Zeiss operating microscope. A 4-mm infusion cannula attached to a reservoir of balanced salt solution (BSS; Alcon, Fort Worth, Tex.) was inserted into the vitreous cavity. Vitrectomy was performed with a Daisy vitrectomy system (Model D1700; Stortz Instruments, St. Louis, Mo.) to facilitate cell attachment on the retina. As much vitreous was removed as possible. The sclerotomy and overlying conjunctiva were closed with 6-0 vicryl sutures. Topical antibiotic ointment was applied to the eyes of each animal to minimize the risk of postoperative infection.

One week after vitrectomy, group A (n=6) received an injection into the vitreous cavity of $2.5 \times 10^4$ non-transduced homologous RDFs in 0.1 ml of BSS and 0.1 ml of G1BgSvNa supernatant ($1.3 \times 10^6$ cfu/ml) containing 10 µg of protamine sulfate (Sigma Chemical Co.). Group B (n=5) received an injection into the vitreous cavity of $2.5 \times 10^4$ homologous lacZ transduced (100%) RDFs in 0.1 ml of BSS and 0.1 ml of DMEM-10. Group C (n=4) received an injection into the vitreous cavity of 0.1 ml of G1BgSvNa supernatant ($1.3 \times 10^6$ cfu/ml) containing 10 µg of protamine sulfate and 0.1 ml of BSS without RDFs.

For histochemical examination, all animals of each group were sacrificed one week after injection. Clinical severity of PVR was graded from stage 0 to 5 according to a previously published classification (Fastenberg et al., *Am. J. Ophthalmol.*, Vol. 93, pgs. 565–572 (1982)) and reviewed by Hida et al., *Graefe's Arch. Clin. Exp. Ophthalmol.*, Vol. 225, pgs. 303–307 (1987). Such classification is given in Table 1 below.

TABLE 1

CLASSIFICATION OF EXPERIMENTAL PVR

| Stage | Characteristics |
| --- | --- |
| 0 | No proliferative changes |
| 1 | Intravitreous membrane |
| 2 | Focal traction; localized vascular changes; hyperemia; engorgement; dilation; blood vessel elevation |
| 3 | Localized detachment of medullary ray |
| 4 | Extensive retinal detachment; total medullary ray detachment with peripapillary retinal folds |
| 5 | Total retinal detachment; retinal folds and holes |

To evaluate lacZ-positive reaction in the eyes, the eyes were enucleated and fixed in 2% paraformaldehyde and 0.4% glutaraldehyde in 0.1 M phosphate buffer (pH 7.3) for 2 hr. The anterior segments and lenses were removed, and the eye cups were incubated at room temperature for 12 hr in a solution of 2 mM $K_3Fe(CN)_6$ 2 mM $K_4Fe(CN)_6$, 2 mM $MgCl_2$, and 2 mg/ml 5-bromo-4-chloro-3-indolyl-b-D-galactoside (X-gal; Gibco, Life Technologies) in phosphate-buffered saline at pH 7.3.

Pictures of the exposed stained fundus were taken with a 35-mm camera. The lacZ-positive areas were digitized through a scanner (Scan Jet IIc; Hewlett-Packard Co., Camas, Wash.) and entered into a computer (MacIntosh; Apple Computer, Cupertino, Calif.). Relative lacZ-positive areas were measured with an image-analyzing software (Image; NIH, Research Service Branch). Relative transduction efficiency was calculated as follows; lacZ-positive areas in group A (in vivo transduction of RDFs with G1BgSvNa)/ lacZ-positive areas in group B (intravitreal injection of lacZ-transduced RDFs) X 100(%).

For light microscopy, the eyes in group C were fixed in half-strength Karnovsky's solution (2.5% glutaraldehyde and 2% formaldehyde) in 0.1 M cacodylate buffer (pH 7.4) for an additional 48 hr. The tissues were dehydrated in a series of graded alcohols and embedded in glycol methacrylate. Two- to three-micrometer sections were stained with periodic acid-Schiff.

Figure 3A:
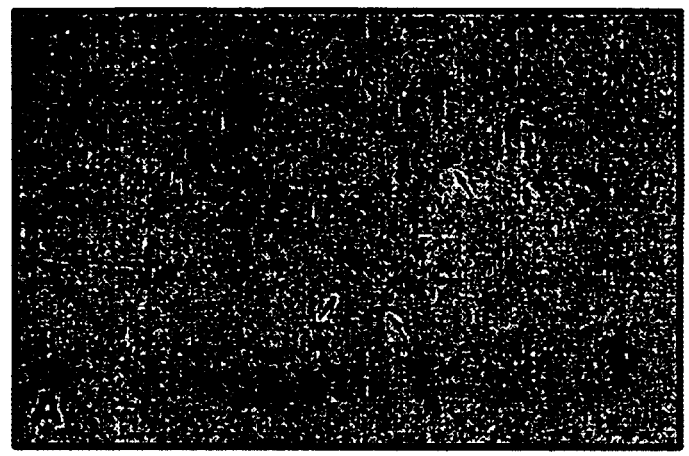
FIGS. 3A and 3B are photographs of the exposed fundus of the eyes of rabbits that received (i) non-trandsduced rabbit dermal fibroblasts and G1BgSvNa vector supernatant, or (ii) rabbit dermal fibroblasts previously transduced with G1BgSvNa, respectively and were stained with X-gal.
Figure 3B:
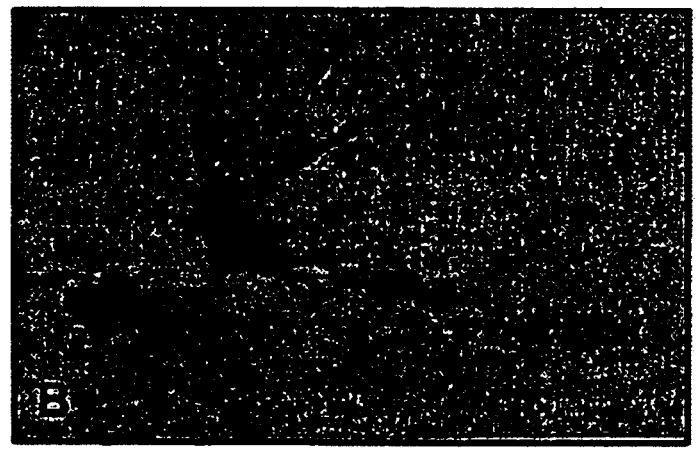

In vivo transduction with G1BgSvNa was performed to study the feasibility of retroviral vector-mediated gene transduction in the vitreous cavity. One week after injection, all eyes receiving fibroblasts (group A and B) developed PVR; there was no statistical difference between the stage of PVR in group A (in vivo transduction of RDFs with G1BgSvNa) and group B (intravitreal injection of lacZ-transduced RDFs). In group A, small numbers of cells showed lacZ expression in preretinal or intravitreous membranes which contracted the retina or induced retinal detachment (FIG. 3A). All preretinal or intravitreous membranes in group B showed more prominent lacZ expression (FIG. 3B). The stage of PVR and the relative lacZ-positive area of the eyes in group A and group B are listed in Table 2.

TABLE 2

PVR STAGE AND LACZ POSITIVE AREA OF THE EYES OF GROUP A AND GROUP B

| Rabbit No. | Stage | LacZ Positive Area (mm$^2$) |
| --- | --- | --- |
| Group A* | | |
| 1 | 5 | 0.67 |
| 2 | 5 | 0.29 |
| 3 | 4 | 0.19 |
| 4 | 2 | 0.11 |
| 5 | 4 | 0.38 |
| 6 | 1 | 0.15 |
| average | | 0.30 ± 0.21 |
| Group B† | | |
| 1 | 5 | 14.83 |
| 2 | 2 | 7.24 |
| 3 | 5 | 15.66 |
| 4 | 3 | 17.62 |
| 5 | 2 | 12.31 |
| average | | 13.53 ± 4.00 |

Figure 4:
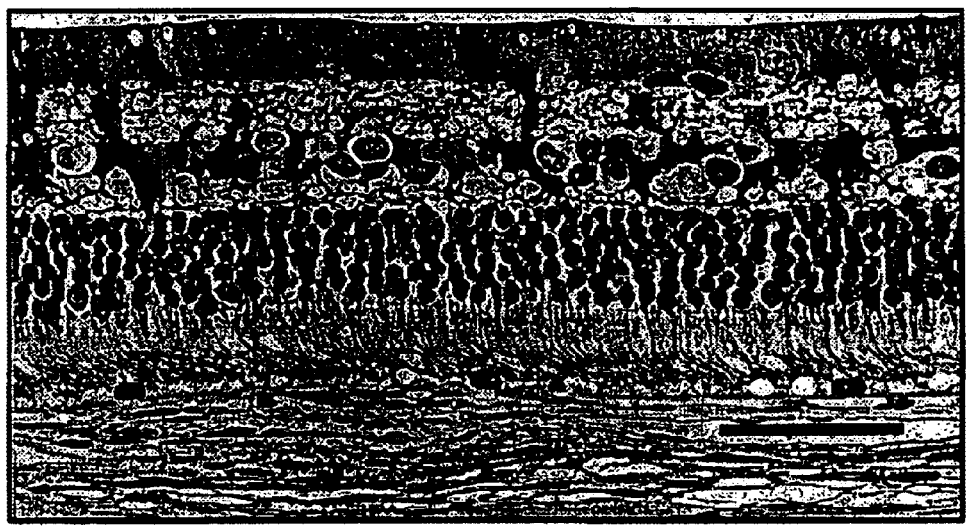
FIG. 4 is a light micrograph of the eye of a rabbit which received the G1BgSvNa vector without rabbit dermal fibroblasts.

*in vivo transduction of RDFs with G1BgSvNa
†intravitreal injection of lacZ-transduced RDFs † intravitreal injection of lacZ-transduced RDFs The relative transduction efficiency was approximately 2% (2.2±1.6%) There were no lacZ-positive reactions in the eyes of group C (intravitreal injection of G1BgSvNa without RDFs). Light microscopic examination of group C showed excellent preservation of the retina, without retinal degeneration or inflammatory cell infiltration (FIG. 4).

Example 5

In vivo Bystander Effect in Experimental Proliferative Vitreoretinopathy

The right eye was used from each of 20 pigmented rabbits of both sexes, weighing 2.5 to 3.5 kg each. Vitrectomy was performed in the same manner as described above. One week after vitrectomy, group D (n=7) received an injection into the vitreous cavity of a mixture of $0.25 \times 10^4$ homologous HSV-tk positive RDFs (5% of total cells) and $4.75 \times 10^4$ homologous HSV-tk negative RDFs (95% of total cells). Group E (n=7) received a mixture of $0.05 \times 10^4$ homologous HSV-tk positive RDFs (5% of total cells) and homologous $4.95 \times 10^4$ HSV-tk negative RDFs (95% of total cells). Group F (n=6) received $5.0 \times 10^4$ homologous HSV-tk negative RDFs as a control. All eyes received 200 µg of ganciclovir (0.1 ml of solution dissolved in distilled water) just after the cell injection and on day 4. Indirect ophthalmoscopic examinations were performed in a masked fashion on days 4, 7, 14 and 28. Clinical severity of PVR was graded from 0 to 5 as described above.

Figure 5A:
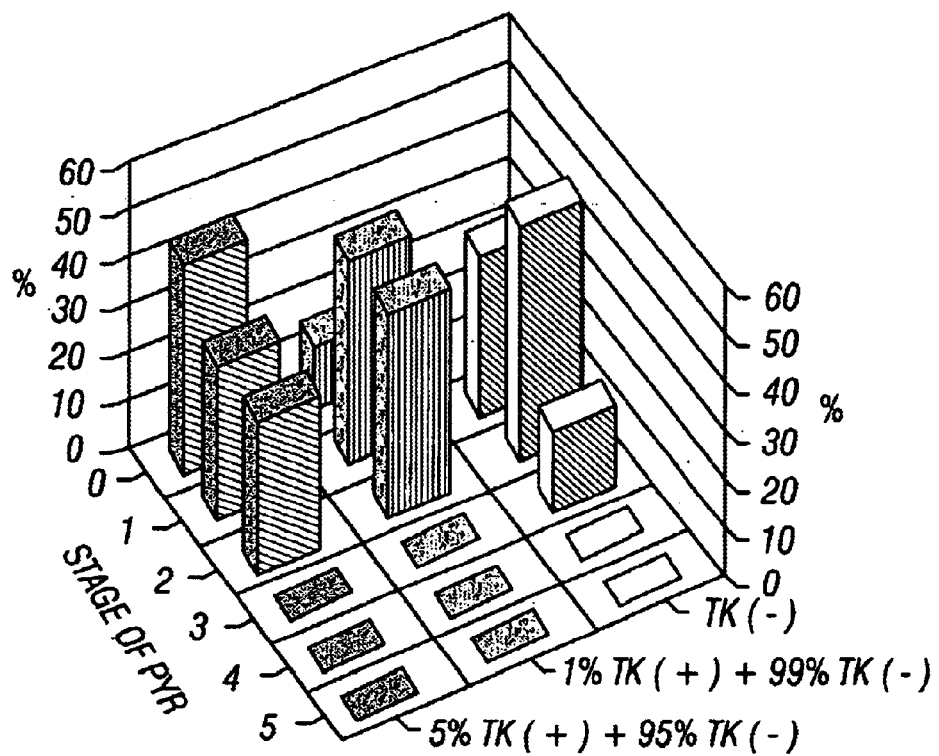
FIGS. 5A, 5B, 5C, and 5D are graphs of the stages of induced proliferative vitreoretinopathy (PVR) in the eyes of rabbits given mixtures of HSV-tk positive and HSV-tk negative rabbit dermal fibroblasts.
Figure 5B:
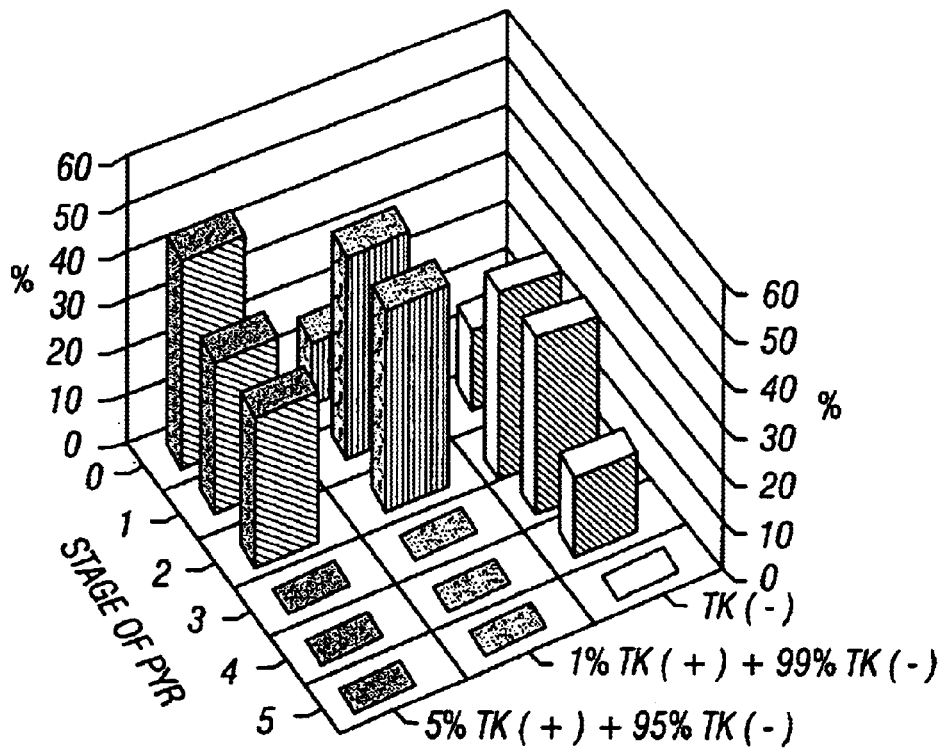
Figure 5C:
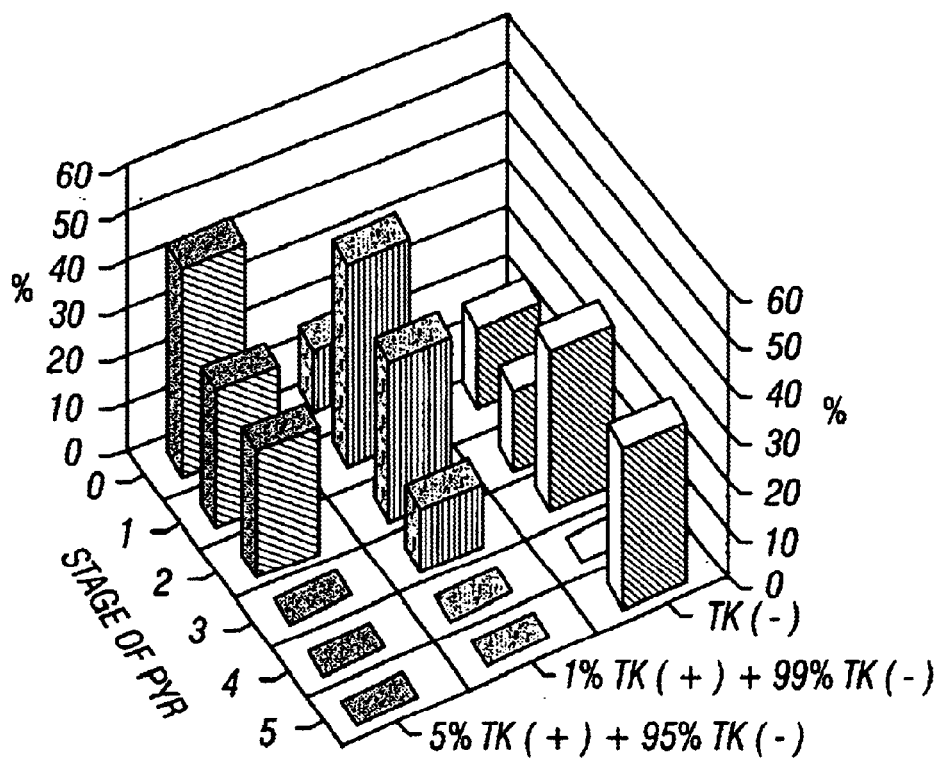
Figure 5D:
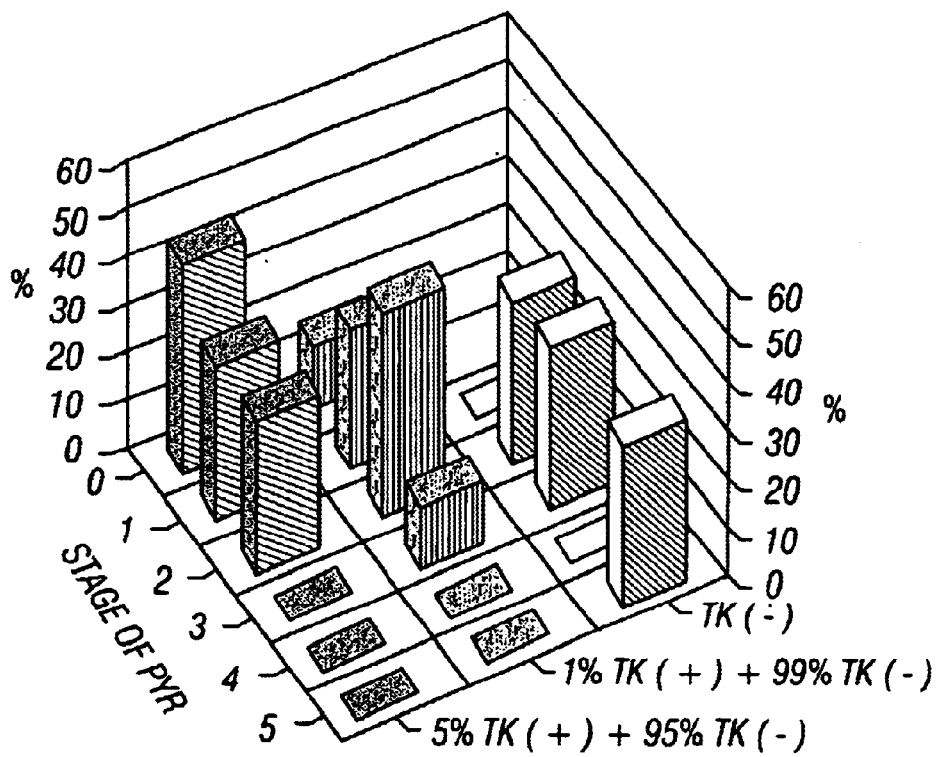

On day 4 and day 7 (FIGS. 5A and 5B), group D (5% HSV-tk positive RDFs) and group E (1% HSV-tk positive RDFs) showed no retinal detachment (stages 3–5) while 1 in 6 eyes (16.7%) and 3 in 6 eyes (50%) in group F (100% HSV-tk negative RDFs) developed retinal detachment on day 4 and day 7, respectively. There was a statistically significant difference between the PVR stages in group D and in group F on day 7 (P=0.02). On day 14 and day 28 (FIGS. 5C and 5D), 1 in 7 eyes (14.3%) in group E and 4 in 6 eyes (66.7%) in group F showed retinal detachment. No eyes showed retinal detachment in group D (P=0.02). The difference between the PVR stages in group D and in group F was also statistically significant on day 14 (P=0.02) and day 28 (P=0.007). Also, there was a statistical difference between the stages of PVR in group E and in group F on day 28 (P=0.03).

Example 6

In vivo Transduction with G1Tk1SvNa and Treatment with Ganciclovir in Experimental Proliferative Vitreoretinopathy The right eye was used from each of 20 pigmented rabbits of both sexes, weighing 2.5 to 3.5 kg each. Proliferative vitreoretinopathy was induced by a modification of the method described by Chandler et al., *Graefe's Arch. Clin. Exp. Ophthalmol.*, Vol. 224, pgs. 86–91 (1986). Briefly, all eyes underwent vitreous compression after injection of 0.4 ml sulfur hexafluoride gas. A paracentesis was performed prior to injection to prevent elevation of the intraocular pressure. The gas expanded, gradually compressed the vitreous humor, and was resorbed within two weeks. Two weeks after gas injection, all eyes received an injection into the vitreous cavity of $2.5 \times 10^4$ homologous RDFs in 0.1 ml of BSS. Thereafter, group G (n=10) received an intravitreal injection of 0.1 ml G1Tk1SvNa serum-free supernatant ($2 \times 10^8$ cfu/ml) containing 10 µg of protamine sulfate. Group H (n=10) received an intravitreal injection of 0.1 ml G1XSvNa serum-free supernatant ($1 \times 10^8$ cfu/ml) containing 10 µg of protamine sulfate as a control. All eyes received 200 µg of GCV on the following day and again on day 4. Indirect ophthalmoscopic examinations were performed in a masked fashion on days 7, 14 and 28. Clinical severity of proliferative vitreoretinopathy was graded from 0 to 5 as described above.

Figure 6:
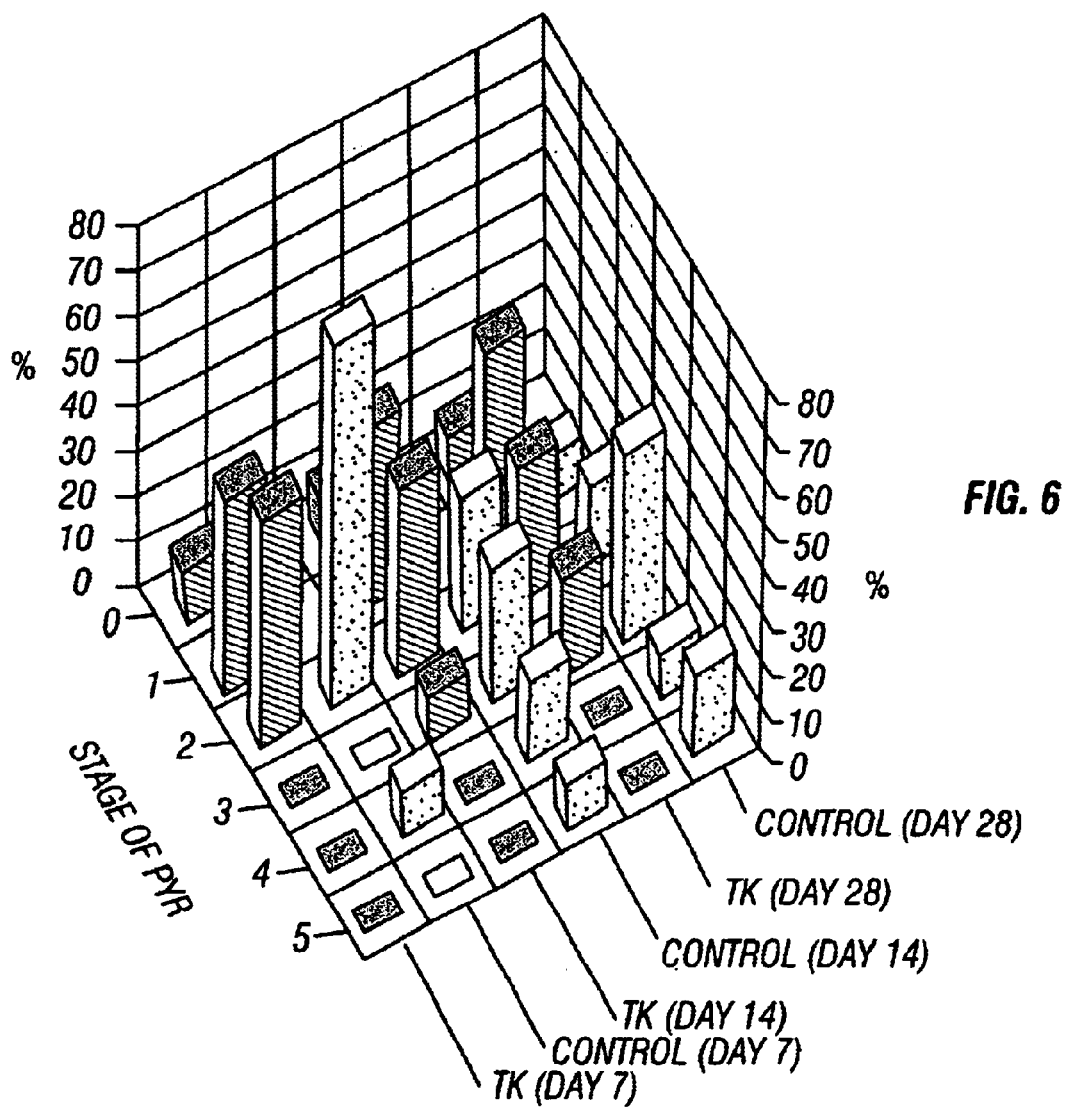
FIG. 6 is a graph of the stages of induced PVR in the eyes of rabbits given non-transduced rabbit dermal fibroblasts, followed by intraocular administration of G1TK1SvNa, followed by administration of ganciclovir.

On day 7, there was significant inhibition of the proliferative vitreoretinopathy stage attained in group G (G1TkSvNa) compared to group H (G1XSvNa) (P=0.04). The differences between the groups were even more striking on day 14 (P=0.01) and remained highly significant at day 28 (P=0.02). Although retinal detachment (stages 3–5) was more frequent in group H at each of the experimental days, the differences did not attain statistical significance (day 14, P=0.06; day 28, P-0.17). It is noteworthy, however, that while 3 of 10 eyes (30%) in group H (G1XSvNa) showed advanced retinal detachment (stages 4 and 5) at day 28, none of those in group G (G1TkSvNa) showed this degree of retinal detachment. FIG. 6 shows the time course of PVR in both group G and group H.

Example 7

In vivo Administration of G1TK1SvNa to Human Patients

Prior to administration of the G1TK1SvNa retroviral vectors, each patient undergoes a three-port vitrectomy to remove as much of the vitreous humor from within the eye as possible. This is accomplished first by removing the conjunctiva from the eye wall in order to expose bare sclera 3 to 4 mm posterior to the limbus (the circular line at the periphery of the cornea). A 20 gauge incision (sclerotomy) is made in the inferotemporal quadrant and an infusion cannula is sewn into place in this incision. This cannula infuses sterile saline into the eye throughout the procedure in order to maintain a normal intraocular pressure. Two similar sclerotomies are made in the superonasal and superotemporal quadrants in order to provide ports of access into the eye. A fiberoptic light source is placed into the eye through one of these ports and a microvitrector device is placed into the eye through the other port. The vitrector is a 20 gauge instrument which alternatively aspirates and cuts vitreous at rates exceeding 700 cycles per minute. First, the core vitreous humor is removed, and then the vitreous humor which is apposed to the retinal surface (i.e., the cortical vitreous humor) is removed. Following the removal of the vitreous humor, any membranes which may be producing retinal traction and detachment are dissected from the retinal surface. After all traction on the retina has been released, the retina may be treated with spots of argon laser light to promote the formation of chorio-retinal adhesions which will reduce the likelihood of future detachments. The eye then may be filled with a gas (sulfurhexafluoride or perfluoropropane) to provide a temporary tamponade of the retina against the eye wall. All three sclerotomies are closed with absorbable sutures. The conjunctiva is closed in a similar fashion, and the eye receives subconjunctival injections of Ancef (25 mg) and Decadron (12.5 mg).

Prior to the injection of materials into the vitreous cavity, the eye which is to be treated receives a subconjunctival injection of 0.1 cc of 1% lidocaine without epinephrine, approximately 4 mm posterior to the limbus. The patient then applies gentle pressure to this area through closed eyelids for three minutes. After ensuring that adequate anesthesia has been achieved, a single drop of Betadine is placed in the conjunctival fornix. A 30 gauge needle on a 1 cc syringe then is introduced into the vitreous cavity through the sclera at a site 3 to 4 mm posterior to the limbus. This is achieved with direct visualization using a binocular indirect ophthalmoscope. Up to 0.5 cc of fluid then is injected over 1 to 2 seconds. The needle is removed and a sterile cotton swab is placed over the entry site. A single drop of topical antibiotic is instilled into the eye following the completion of the injection.

Patients are treated with viral supernatant containing the retroviral vector G1TK1SvNa at Dose Level I (concentration of G1TK1SvNa of $1 \times 10^6$ cfu/ml, maximum volume 0.1 ml), Dose Level II (concentration of G1TK1SvNa of $5 \times 10^6$ cfu/ml, maximum volume 0.1 ml), or Dose Level III (concentration of G1TK1SvNa of $1 \times 10^7$ cfu/ml, maximum volume 0.1 ml). Initially, three patients receive G1TK1SvNa by intraocular injection at Dose Level I, in an amount not exceeding 0.1 ml. The vector also is administered at day 2 and day 4 after vitrectomy. If no more than one of three patients at Dose Level I develops a grade 3 or grade 4 adverse toxicity event which appears to be related to the administration of G1TK1SvNa, then two additional patients will be enrolled at Dose Level I. Adverse ocular toxicity events are graded as follows:

Grade 1: Vitreous haze.

Grade 2: Acute increase in ocular pressure (>45 mm Hg for >20 min.)

Persistent pain (>5 min.)

Vitreous hemorrhage (small, localized).

Grade 3: Lens opacification
Acute retinitis
New retinal break
Vitreous hemorrhage (large, diffuse)
Grade 4: Acute retinal detachment
Acute vein or arterial occlusion
Suppurative infection
Acute and persistent loss of vision (three or more lines on the Snellen visual acuity chart), except as with vitreous hemorrhage.

If none of the first three, or two of five patients treated at Dose Level I, develop a grade 3 or 4 adverse event which appears to be related to the G1TK1SvNa retroviral vector, the dose of retroviral vector will be escalated to the next dose level(s).

The treatment plan is identical to the one described for Dose Level I. The Maximum Tolerated Dose (MTD) is defined as one dose level below the level at which dose limiting toxicity is observed.

On each of days 8, 9, and 10 of the treatment, each patient is given an intraocular injection of up to 1 mg of ganciclovir (Syntex Corp., Palo Alto, Calif.).

At day 22, and at weeks 5, 8, and 12, each patient receives a full ocular examination. After twelve weeks, each patient receives a complete ocular examination at eight-week intervals through week 102. Each patient also is evaluated for retroviral transfer safety monitoring at post-treatment weeks 4, 8, and 12, then every 12 weeks for the remainder of one year, and at least annually for life thereafter.

The disclosure of all patents, publications (including published patent applications), and database entries referenced in this application are specifically incorporated herein by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A method of treating a human patient having proliferative vitreoretinopathy, comprising:
   (a) providing by intravitreal administration a retroviral vector in an amount sufficient to transduce replicating ocular cells in said human patient in vivo, wherein the retroviral vector comprises a polynucleotide encoding Herpes Simplex Virus thymidine kinase wherein said Herpes Simplex Virus thymidine kinase is expressed in an amount effective to provide for the inhibition, prevention, or destruction of the growth of replicating ocular cells upon administration of ganciclovir to said human patient; and
   (b) administering to said patient ganciclovir in an amount effective to interact with said Herpes Simplex Virus thymidine kinase in order to inhibit, prevent, or destroy the growth of said replicating ocular cells.

2. The method of claim 1 wherein said retroviral vector is administered in an amount of from about $10^4$ cfu/dose to about $10^8$ cfu/dose.

3. The method of claim 1 wherein said ganciclovir is administered intraocularly.

4. The method of claim 1 wherein said ganciclovir is administered in an amount of from about 20 µg/eye/dose to about 1 mg/eye/dose.

5. The method of claim 1 wherein said ganciclovir is administered to the vitreous cavity of the eye.

6. A method of treating a subject having proliferative vitreoretinopathy, comprising:
   (a) introducing into said subject, via intravitreal administration, a retroviral vector comprising a polynucleotide encoding thymidine kinase, wherein replicating ocular cells are transduced with said polynucleotide, and wherein said thymidine kinase is expressed in said replicating ocular cells; and
   (b) administering ganciclovir to said subject in amount effective to interact with said thymidine kinase expressed in said replicating ocular cells, wherein said interaction results in the inhibition of intraocular cellular proliferation.

7. The method of claim 6 wherein said retroviral vector is administered in an amount of from about $10^4$ cfu/dose to about $10^8$ cfu/dose.

8. The method of claim 6 wherein said thymidine kinase is selected from the group consisting of Herpes Simplex Virus thymidine kinase, cytomegalovirus thymidine kinase, and varicella-zoster virus thymidine kinase.

9. The method of claim 6 wherein said thymidine kinase is Herpes Simplex Virus thymidine kinase.

10. The method of claim 6 wherein said ganciclovir is administered intraocularly.

11. The method of claim 6 wherein said ganciclovir is administered in an amount of from about 20 µg/eye/dose to about 1 mg/eye/dose.

12. The method of claim 6 wherein said ganciclovir is administered to the vitreous cavity of the eye.

13. A method of treating a human patient having an ocular disorder involving intraocular cellular proliferation, comprising:
   (a) administering intraocularly a retroviral vector in an amount sufficient to transduce replicating ocular cells in said human patient in vivo, wherein the retroviral vector comprises a polynucleotide encoding a thymidine kinase wherein said thymidine kinase is expressed in an amount effective to provide for the inhibition, prevention, or destruction of the growth of replicating ocular cells upon administration of ganciclovir to said human patient; and
   (b) administering to said patient ganciclovir in an amount effective to interact with said thymidine kinase in order to inhibit, prevent, or destroy the growth of said replicating ocular cells.

* * * * *

UNITED STATES PATENT AND TRADEMARK OFFICE
CERTIFICATE OF CORRECTION

PATENT NO. : 6,869,935 B2
DATED : March 15, 2005
INVENTOR(S) : David Hinton, W. French Anderson and Stephen J. Ryan It is certified that error appears in the above-identified patent and that said Letters Patent is hereby corrected as shown below:

Column 1,
Line 3, insert -- This invention was made with government support under Contract Nos. R01-EY02061 and EY03040 awarded by the National Institutes of Health. The government has certain rights in the invention. --

Signed and Sealed this

Thirty-first Day of May, 2005

JON W. DUDAS
*Director of the United States Patent and Trademark Office*